United States Patent
Telxelra Moretra et al.

(10) Patent No.: US 6,872,224 B1
(45) Date of Patent: Mar. 29, 2005

(54) INTRODUCER AND PLACER OF REPAIRS IN TUBULATIONS

(76) Inventors: Luciano José Telxelra Moretra, R. Tomaz de Aquino, 149, Florianópolis (BR), 88036-560; Ricardo Machado Peres, R. Lauro Llnhares, 689 BL04/203, Florianópotis (BR); Pierre Galvagni Silveira, 401 KM 01 Celta/Nano, Florianópolis (BR), 88030-000

( * ) Notice: Subject to any disclaimer, the term of this patent is extended or adjusted under 35 U.S.C. 154(b) by 0 days.

(21) Appl. No.: 09/980,742
(22) PCT Filed: Apr. 26, 2000
(86) PCT No.: PCT/BR00/00042
§ 371 (c)(1),
(2), (4) Date: Oct. 19, 2001
(87) PCT Pub. No.: WO00/65270
PCT Pub. Date: Nov. 2, 2000

(30) Foreign Application Priority Data

Apr. 26, 1999 (BR) .............................. 9900959

(51) Int. Cl.$^7$ ................................................. A61F 2/06
(52) U.S. Cl. ...................... 623/1.12; 623/1.23; 606/108
(58) Field of Search ............................... 623/1.12, 1.11, 623/1.23, 2.11; 606/108, 109

(56) References Cited

U.S. PATENT DOCUMENTS

| | | | | |
|---|---|---|---|---|
| 4,665,918 A | * | 5/1987 | Garza et al. ................. | 606/108 |
| 5,683,451 A | * | 11/1997 | Lenker et al. ............. | 623/1.11 |
| 6,183,443 B1 | * | 2/2001 | Kratoska et al. ....... | 604/164.03 |

* cited by examiner

Primary Examiner—Michael H. Thaler
(74) Attorney, Agent, or Firm—Hedman & Costigan, P.C.

(57) ABSTRACT

INSERTER AND FITTER OF TUBING REPAIR SETS characterized by being a tubular shape mechanical device, rigid or flexible, having a receptacle for housing a tubing repair set(12) also called prosthesis(12) with handles (8)(9) to insert and fit the prosthesis(12) at a target place. Having a nose cone(1) which leads the way to the catheter; a hooking system(5)(11) of the prosthesis(12) with a trigger (10) to loose and place the prosthesis at the target place inside the tubing.

11 Claims, 6 Drawing Sheets

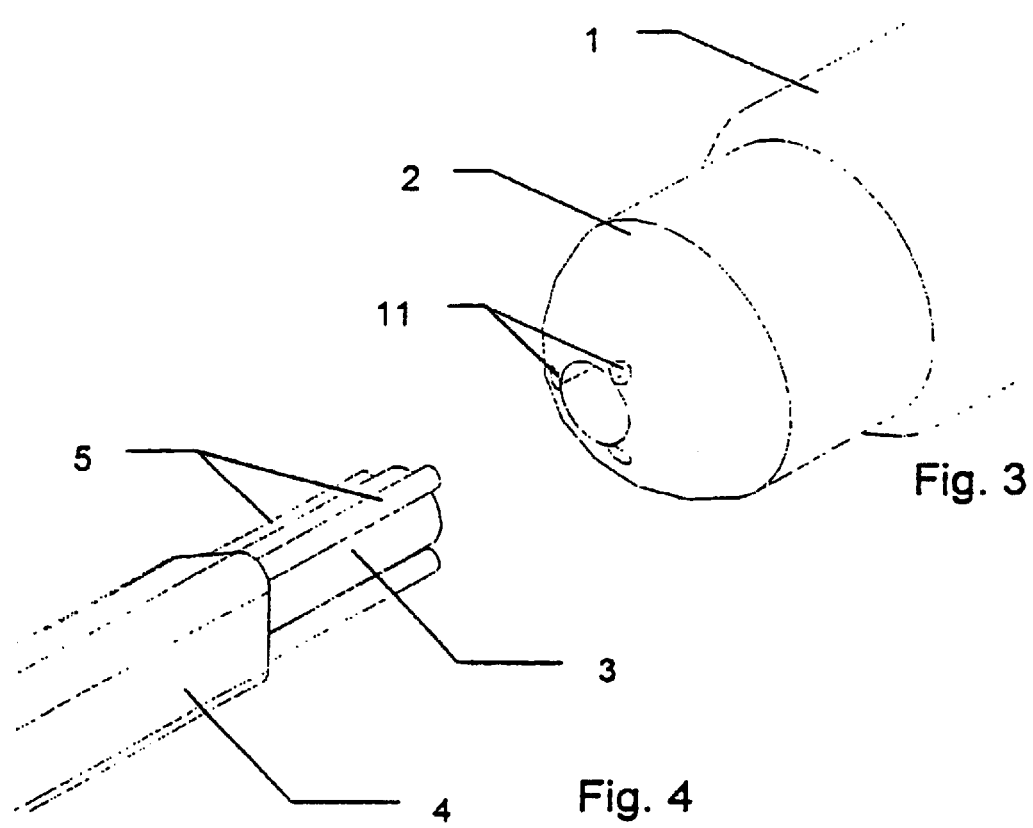

INTRODUCER AND PLACER OF REPAIRS IN TUBULATIONS

It is related to a tubular shape mechanical device having a receptacle in which a tubing repair set is stored, with controls to insert and fit the repair set at a target place of a tubing inner wall.

Sometimes in medicine there is the necessity of fitting repair sets, called prosthesis, in the blood circulating system tubing or in the digestive system tubing. There already are many apparatus, called catheter, to insert and fit the prosthesis at a specific place in the blood vessels inner wall, veins and other ones. The using of these apparatus together with imaging devices is called treatment or minimum invasive surgery, just because there is no need of submitting the patient to extremely large and traumatic incisions.

The endoprostheses usage by means of the minimum invasive surgery has been increasing lately and presently there are many worldwide enterprises, such as World Manufacturing Corporation and Braile Corporation, that have their own design and that manufacture these apparatus to treat deceases in the vascular system, breathing system or digestive system, that is, the human body tubing systems. Nevertheless, the existing endoprostheses have problems related to positioning, to the fluid flow during its placing, shortening of its length and other ones.

These existing endoprostheses have a small height cylinder shape formed by a sequence of interconnected rings. Each ring being formed by a zigzag bent wire forming a small height cylinder. A collection of these rings are jointed and coated by a biocompatible polymeric fabric. The endoprostheses so manufactured have the characteristic not to offer resistance to axial compression forces. When the small height cylinder, which is the prostheses itself, is submitted to a compression force it is shortened; the rings are juxtaposed due to its wire framed structure.

The existing catheters characterize by having a tubing, here called sheath, inside of which the prosthesis is placed; it is previously radially compressed previously staying like that inside the sheath. A catheter is inserted inside the artery or any other tubing inside the human body. The catheter is inserted until the sheath distal end reaches the point where the prosthesis is to be placed. The prosthesis is then removed from inside the catheter by the action of an existing piston inside the sheath, which pushes the prosthesis out of the sheath. The sheath doesn't move. Pushing the prosthesis out causes an axial compression force on the wired rings that form the prosthesis case. The piston action causes such compression force—the axial force on the prosthesis distal end plus the reaction force due to friction caused by the compressed prosthesis against the sheath inner wall. To this reaction force is added the existing obstruction inside the artery. The consequence to this procedure is placing a prosthesis with the length shorter than the desired one and the possibility of fitting it at an inappropriate place. In case this happens, the existing catheters don't have technical resources to replace the prosthesis during its positioning.

Some catheters use the procedure of removing the prosthesis from inside the sheath reverse way, that is, the piston stands still and the sheath that holds the prosthesis is pulled back. As the sheath goes back the prosthesis stands still holded by the piston. While the prosthesis comes out of the sheath, it expands and fits itself at the desired place inside the artery. This procedure shows a technical improvement, as there isn't any prosthesis' axial displacement related to the artery inner wall. Nevertheless, there still is the prosthesis friction related to the catheter sheath inner wall. The prosthesis still is taken out from the catheter by means of a compression force.

Replacing the prosthesis during its positioning still is unviable and traumatic. Once the prosthesis positioning is started, it comes out of the sheath, spreads itself spreading also the artery. When the first ring, close to the distal end of the small height cylinder, comes out the catheter, it spreads and drowns into the artery inner surface, making any other farther movement difficult. Trying to replace the prosthesis by any axial movement would be difficult on account of the obstruction made by the artery wall.

The action of pushing the prosthesis proximal end is an existing catheters general characteristic and may cause the prosthesis shortening, since the prosthesis comprises wired rings that move one upon the other; it may cause a positioning error because the prosthesis tends to jump from inside the catheter due to the rings spring effect. Difficulties in placing a prosthesis at a definite position has required the unnecessary use of longer prosthesis; this may cause another principal artery branch occlusion.

U.S. Pat. No. 5,683,451 is related to same group of catheter that pushes the prosthesis out of it. It includes a plurality of disposed runners 42 affixed together at one of their proximal ends to one of the shaft 34 ends, which push the prosthesis out of the catheter. The runners 34 remain around the prosthesis 10 reducing its sliding resistance related to the sheath 32 inner wall. Doing this the desired technical effect is withdrawing prosthesis 10 out of inside sheath 32 without shortening it. This is also one of the present report purposes. Another acquired technical effect is a better control over the prosthesis radial expansion process procedure while coming out from inside sheath 32. The runners 42 involving the prosthesis 10 avoid the prosthesis sudden expansion.

While the existing catheters are characterized by pushing the prosthesis out of the catheter, the inserter and fitter of tubing repair sets hereby described is characterized by pulling the prosthesis out of the catheter. The prosthesis is hooked up to the catheter dragging wires. These wires track the prosthesis out of the catheter. The prosthesis distal end, which is hooked up to the dragging wires, stays hooked until the whole prosthesis is out of the catheter and placed at the target point inside the artery. During the prosthesis manual tracking out of the catheter it is possible to stop the procedure, visualize and check if the positioning place is the correct and desired one or if it is necessary to move the catheter to a new position carrying the prosthesis that still is held to the catheter by its both ends; the proximal end stays inside the catheter sheath and the distal end stays hooked up to the dragging wires. It is also characterized by having a trigger which holds the prosthesis coupled to the catheter even after the prosthesis withdrawing out of the interior of the catheter. The prosthesis will only by uncoupled from the catheter after the trigger be manually driven.

The inserter and fitter of tubing repair sets hereby described, also called catheter, comprises a tubular device, rigid or flexible, with its outer diameter smaller than the tubing inner diameter, having at its distal end a place to store the repair set, also called prosthesis and having internal cables and rods which can be reached by the opposite side, proximal end, in order to handle and place the repair set inside the tubing.

The figures hereafter described show the device principal functional elements. They don't specify the dimensions and they don't show the real proportionality among the device elements. Not showing proportionality in the drawings is due to the fact that the dimensions and proportionality among the elements vary individually according to the employment, the type and size of the repair set and the tubing inner diameter.

FIG. 3 shows the base(2) of the nose cone(1) with the socket holes(11) to sock the dragging wires(5).

FIG. 4 shows the core shaft(3), the multilumen tubing(4) and the dragging wires(5).

Figure 1:
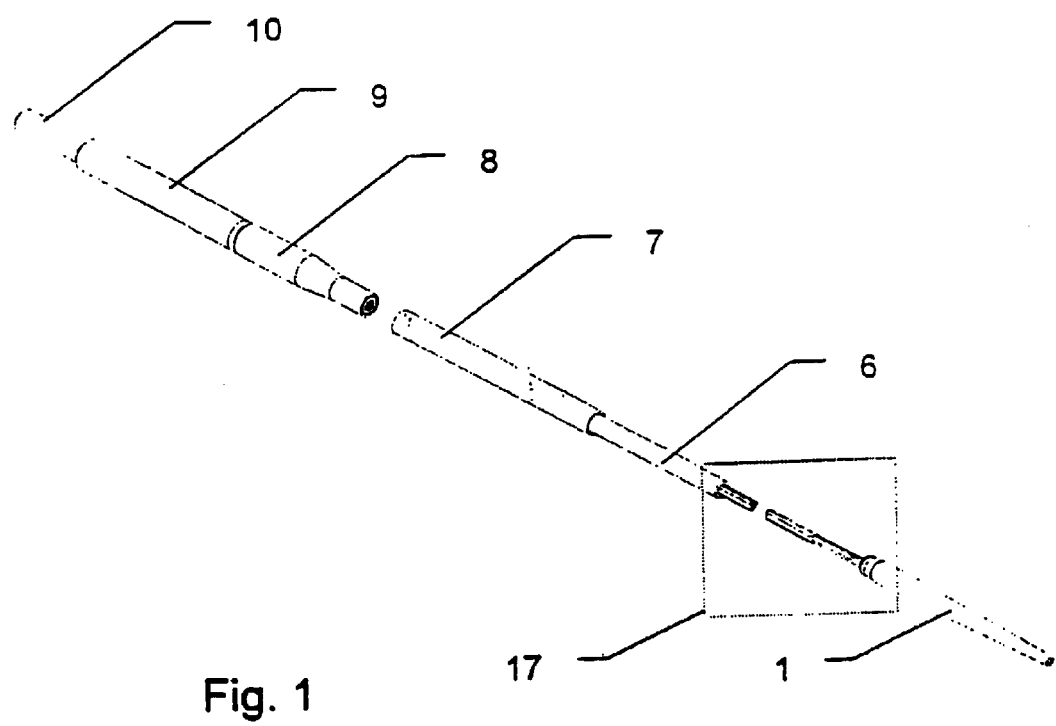
FIG. 1 shows the device comprising the nose cone(1), the spacing tubing(6), the sheath(7), the handle(8) of the sheath (7), the handle(9) of the spacing tubing(6), the trigger(10) and the device particular inside spot(17).
Figure 2:
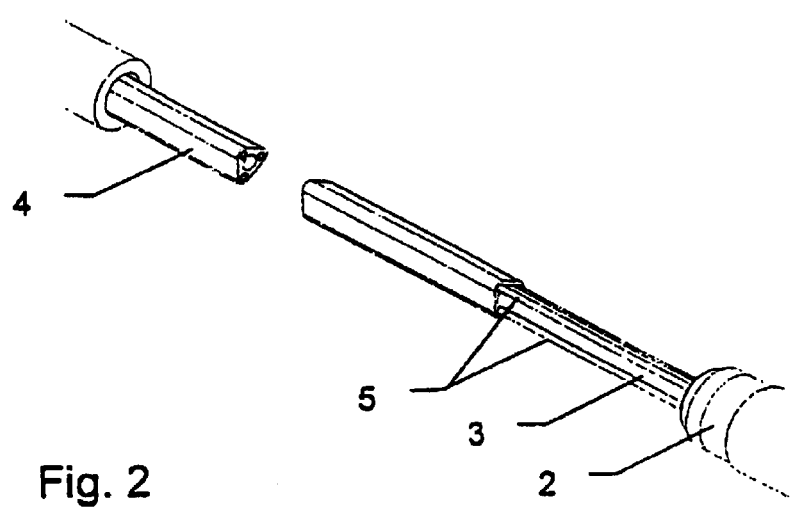
FIG. 2 shows the device particular inside spot(17) enlarged view comprising the base(2) of the nose cone(1), the core shaft(3), the multilumen(4) tubing and the dragging wires(5). The multilumen(4) tubing has longitudinal holes through which slide the dragging wires(5).
Figure 5:
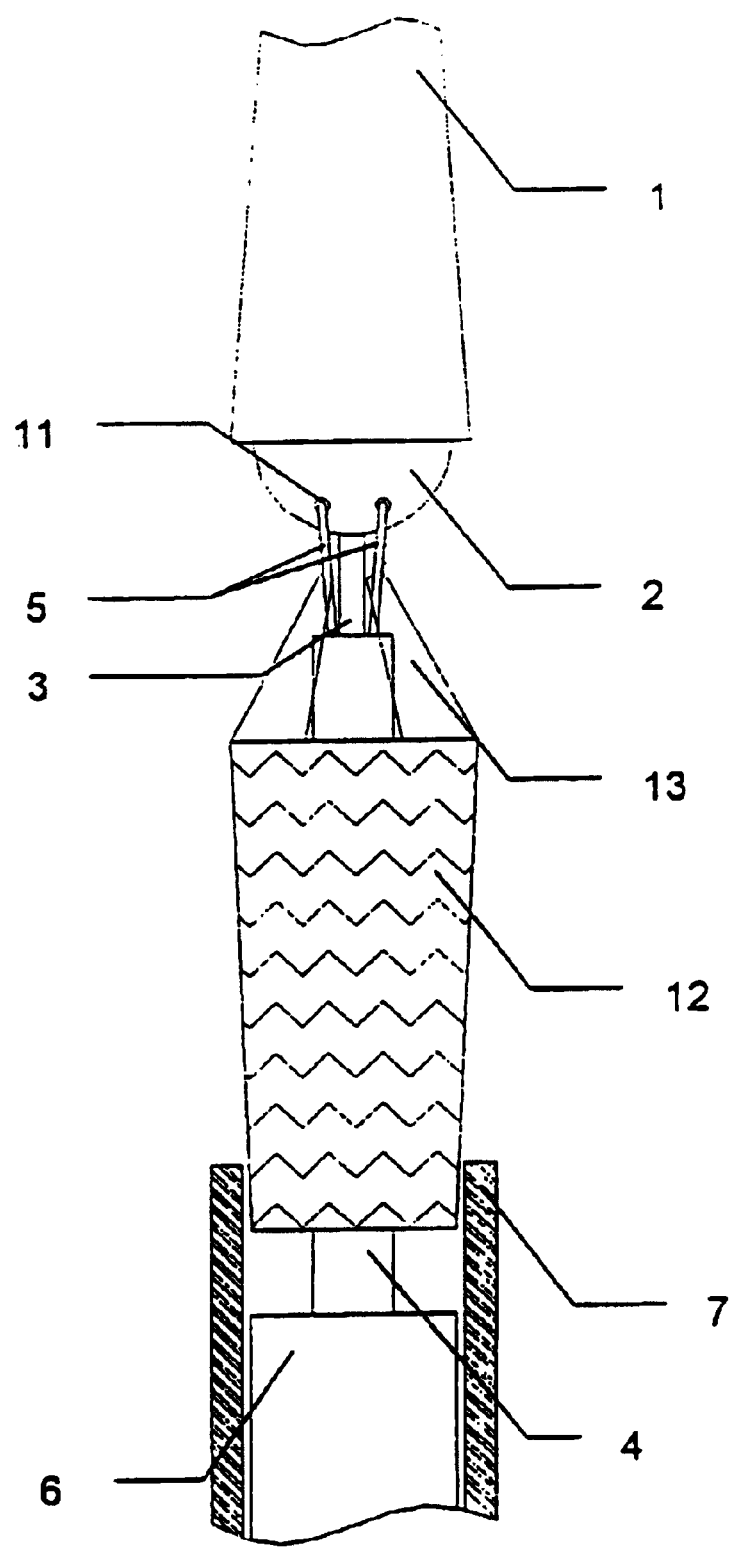
FIG. 5 shows in detail how the prosthesis(12) is hooked up to the dragging wires(5); the dragging wires(5) distal end is inserted in the socket holes(11) in the base(2) of the nose cone(1); the prosthesis(12) wrapping the multilumen tubing (4) and housed inside the sheath(7) and lined up with the spacing tubing(6). The prosthesis(12) has eyelets(13) to hook up and hold the dragging wires(5).
Figure 6:
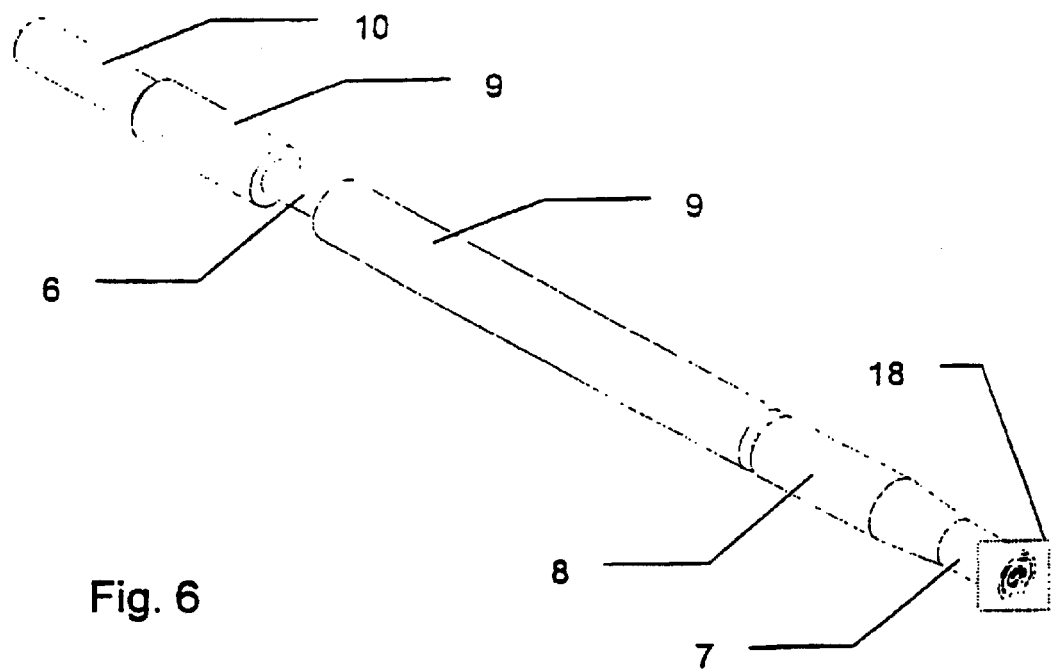
FIG. 6 shows section(18), the sheath(7), the handle(8) of the sheath(7), the handle(9) of the spacing tubing(6) and the trigger(10).
Figure 7:
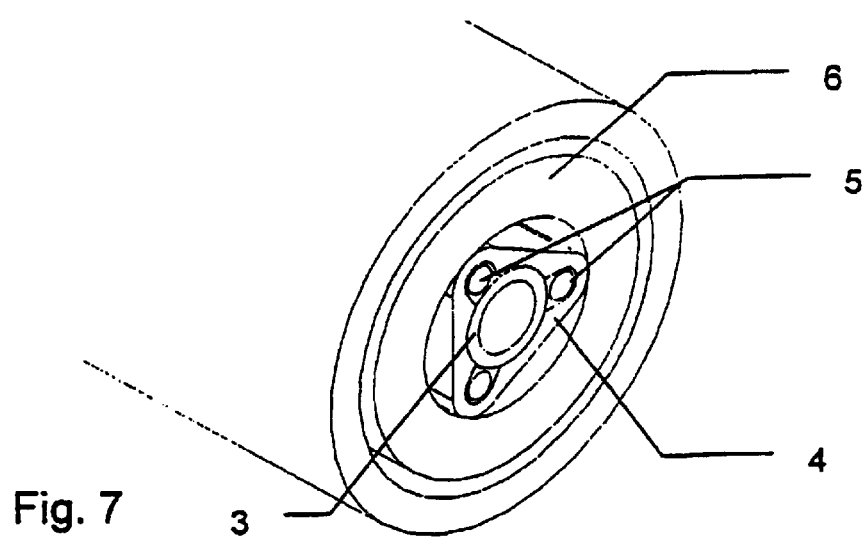
FIG. 7 shows section(18) enlarged view with the core shaft(3), the multilumen tubing(4), the dragging wires(5) and the spacing tubing(6).
Figure 8:
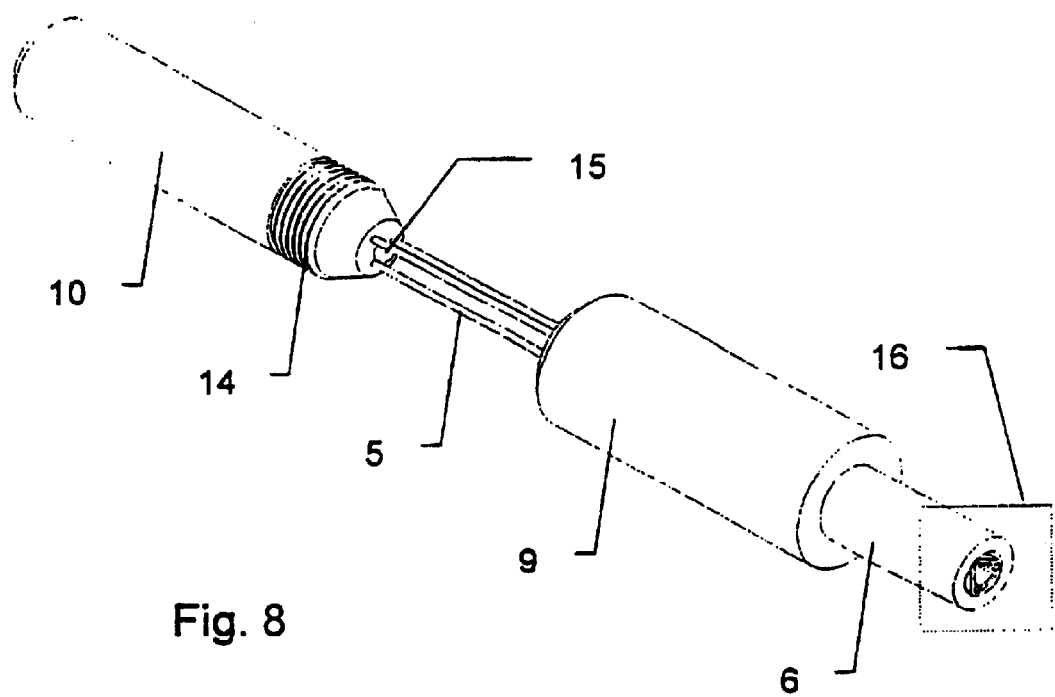
FIG. 8 shows section(16), the handle(9) of the spacing tubing(6), the trigger(10) with the locking screw(14) and the dragging wires(5) fixing spot(15) on the trigger(10).
Figure 9:
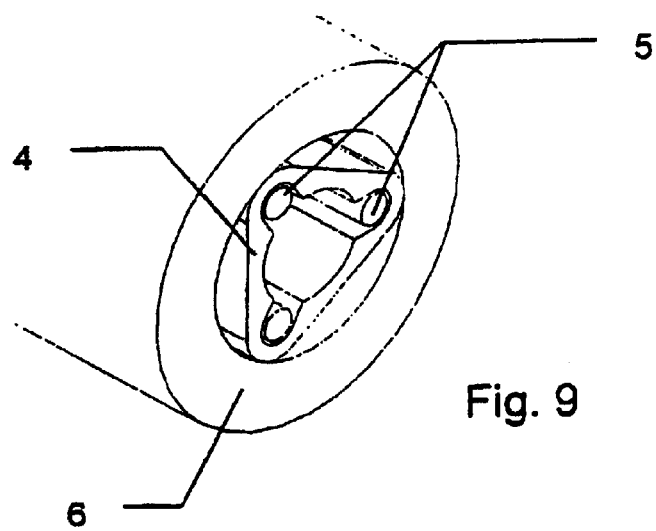
FIG. 9 shows section(16) enlarged view with the multilumen tubing(4), the dragging wires(5) and the spacing tubing(6).
Figure 10:
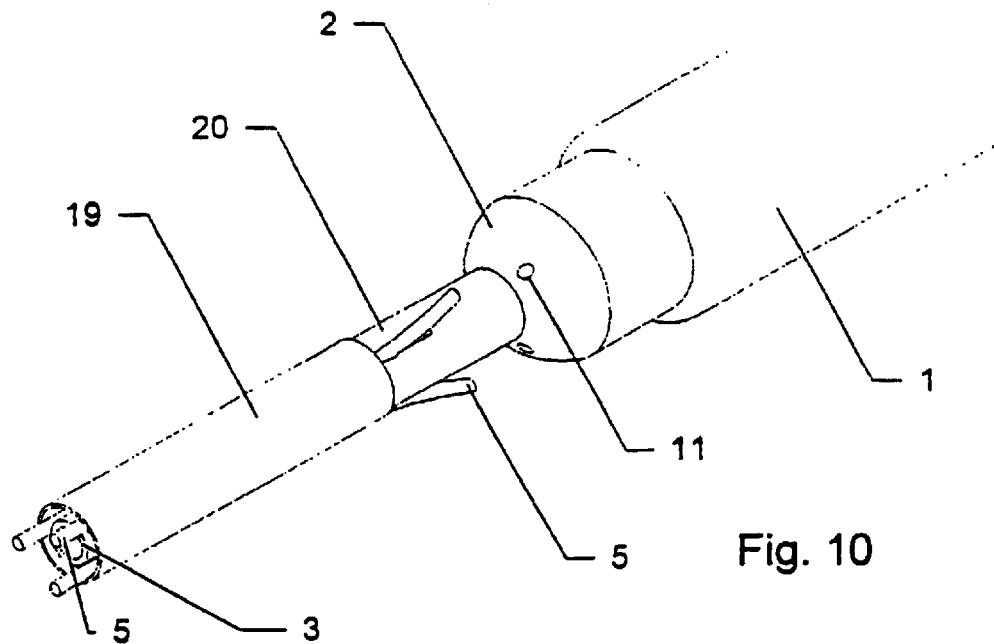
FIG. 10 shows a perspective view where the multilumen tubing(4) is replaced by the cylindrical tubing(19) and connector(20); it also shows the base(2) of the nose cone(1) with the socket holes(11), the core shaft(3) and the dragging wires(5).
Figure 11:
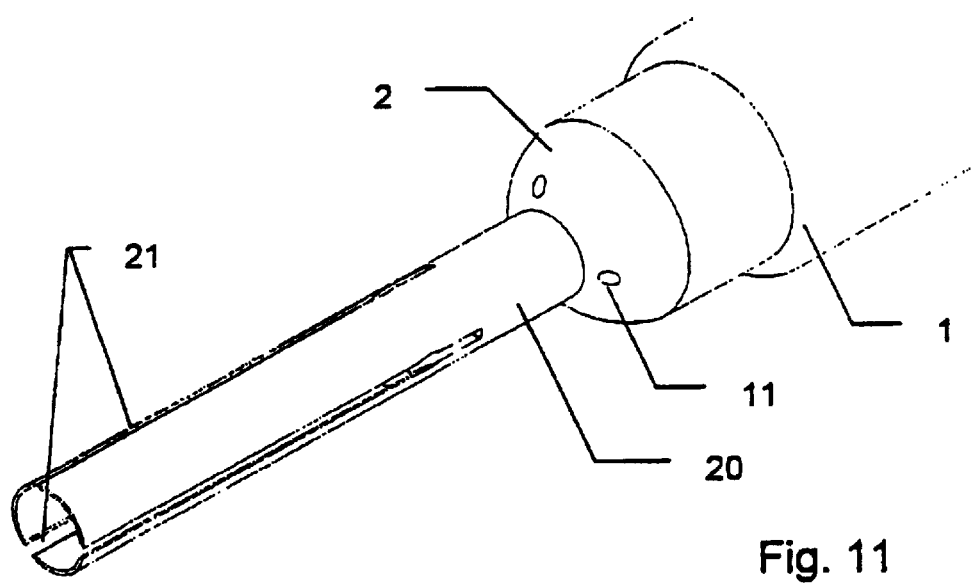
FIG. 11 shows the base(2) of the nose cone(1) with the connector(20) set in the base(2). It shows the chaps(21) of the connector(20).

The repair set is built depending on the employment, type and size of the prosthesis and of the tubing inner diameter. Special attention must be given in building the end point where the prosthesis(12) is going to be stored. The prosthesis(12) is inserted inside the sheath(7), wrapping the multilumen tubing(4), taking the spacing tubing(6) empty space and hooked up through the eyelets(13) to the dragging wires(5). The device is inserted inside the tubing to be repaired, an artery by example, until the prosthesis(12) reaches the tubing damaged place. The delivery distance can be previously set by measuring the distance between the damaged place and the end from which the device is being inserted. Monitoring the placement of the prosthesis(12) can be done by X-rays, ultrasound or other means. Once the prosthesis is positioned at the target place, the sheath(7) is axially withdrawn sliding axially in relation to the spacing tubing(6), in a way that the unit formed by the nose cone(1), core shaft(3), multilumen tubing(4), dragging wires(5), spacing tubing(6) and the prosthesis(12) stand still, freeing the prosthesis(12) from its housing. The prosthesis(12) starts to expand itself until it pressures the tubing under repair inner wall; the prosthesis(12) stays hooked up to the dragging wires(5) by the eyelets(13). At this procedure phase one can evaluate the prosthesis(12) positioning related to the target place; if it is necessary to adjust something one can axially displace the prosthesis(12) by pushing the hole unit, specially the nose cone(1) forward; the prosthesis(12) displaces itself together with the whole unit due to the dragging wires(5) hooked up to the prosthesis(12) eyelets(13). The nose cone(1) has a truncated conical shape staying over a base(2) with a spherical cap shape. Such truncated conical shape was necessary to ease the catheter inward displacement inside the artery; the base(2) spherical cap shape was necessary to ease the catheter outward displacement together with the prosthesis(12) in the case eventual positioning adjustments are necessary alongside the artery. The nose cone(1) has such aerodynamical shape on both sides of its axis in order to reduce the device's friction related to the artery inner wall and to make the surgery less traumatic. The base(2) of the nose cone(1) has a number of socket holes(11) radially allocated equal to the number of the existing dragging wires(5) in which the mentioned dragging wires(5) are socked. At the prosthesis(12) placement procedure, the dragging wires(5)—axially allocated inside the prosthesis (12)—go through the eyelets(13) and are socked in the socket holes(11). They stay there even during the coming out of the prosthesis(12) from inside the catheter. The dragging wires(5) loosening from the socket holes(13) happens only when the trigger(10) is driven. When the adjustment is accomplished the trigger(10) is driven and the dragging wires(5) are gathered inside the multilumen(4) tubing, loosing definitely the prosthesis(12) from the device. The multilumen tubing(4) shown in FIGS. 2,4,5,7 and 9 with a cross-section in a triangular shape, may have a polygonal cross-section with many sides or even a circular one. The multilumen tubing(4) cross-section shape depends on how the prosthesis(12) is built, its folding way and sockets. FIG. 10 shows the circular cross-section cylindrical tubing(19) without any longitudinal drilling to let the dragging wires(5) pass through in the place of the multilumen tubing(4). The dragging wires(5) go loose inside the portion between the core shaft(3) and the smooth cylindrical tubing(19).

The sheath(7) axial retreat is manually achieved, staying the handle(9) of the spacing tubing(6) still and axially displacing the handle(8) of the sheath(7) in direction of the mentioned handle(9) of the spacing tubing(6).

The trigger(10) is a cylindrical rigid handle located at the catheter proximal end; it has a locking screw(14) which is an external threaded short cylindrical surface, that is screwed to the body of the mentioned handle(9) of the spacing tubing (6).

The dragging wires(5), that have their distal end free to be held by the eyelets(13) of the prosthesis(12) in order to sock in the holes(11) of the nose cone(1), have their proximal end fixed to the base(15) of the trigger(10). Driving the trigger(10) means unscrewing the locking screw(14) of the trigger(10) from the handle(9) of the spacing tubing(6) and axially displacing the trigger(10) away from the mentioned handle(9).

Although in the report text and in the figures the sheath (7) is mentioned and shown as a uniform cross-section cylindrical tubing, it can have the geometric shape of a staggered diameters tubing. The staggered tubing end near the nose cone(1) may have the diameter larger than the sheath(7) body in order to house the prostheses that need bigger housing.

What is claimed is:

1. A device for placing a prosthesis into a tubing system comprising:
   (a) a nose cone that comprises a truncated conical portion and a base with socket holes;

(b) a prosthesis that comprises a distal end with eyelets and a proximal end;

(c) a trigger;

(d) dragging wires comprising proximal ends attached to the trigger and distal ends that go through the eyelets of the prosthesis and are socked into the socket holes of the nose cone base; and (e) a sheath that surrounds the prosthesis wherein the dragging wires pull the prosthesis from the sheath.

2. The device as defined in claim 1 wherein the sheath is axially movable with respect to the dragging wires.

3. The device as defined in claim 1 wherein the dragging wires extend axially through an internal lumen of the prosthesis.

4. The device as defined in claim 1 wherein the socket holes are radially allocated in the base of the nose cone and are equal to the number of dragging wires.

5. The device as defined in claim 1 wherein the trigger is a device for removing the dragging wires from the socket holes of the nose cone base and the eyelets of the prosthesis.

6. The device as defined in claim 1 wherein the base of the nose cone has a spherical cap shape.

7. The device as defined in claim 1 further comprising a core shaft that extends through the internal lumen of the prosthesis and the sheath and that comprises a distal end attached to the base of the nose cone and a proximal end that is attached to a handle portion of a spacing tube.

8. The device as defined in claim 7 further comprising a tube that surrounds the core shaft and dragging wires and extends axially through the internal lumen of the prosthesis and the sheath.

9. The device as defined in claim 8 wherein the tube surrounding the core shaft comprises multiple lumens wherein each of the multiple lumens receives one of the dragging wires.

10. A device for placing a prosthesis into a tubing system comprising:

(a) a core shaft comprising a proximal end attached to a handle and a distal end attached to a nose cone wherein the nose cone comprises a truncated conical portion and a spherical cap shaped base with socket holes;

(b) a prosthesis that comprises a distal end with eyelets and a proximal end;

(c) a trigger that is removably attached to the handle of the core shaft;

(d) dragging wires comprising proximal ends attached to the trigger and distal ends that go through the eyelets of the prosthesis and are socked into the socket holes of the nose cone base;

(e) a sheath that surrounds the prosthesis and is axially movable; and (f) a tube that surrounds the dragging wires and core shaft and extends axially through the lumen of the prosthesis and the sheath wherein the dragging wires pull the prosthesis from the sheath.

11. The device as defined in claim 10 wherein the tube comprises multiple lumens wherein each of the multiple lumens receives one of the dragging wires.

* * * * *